(12) United States Patent
McLeod et al.

(10) Patent No.: US 8,282,681 B2
(45) Date of Patent: Oct. 9, 2012

(54) BIORESORBABLE SPINAL IMPLANT AND RELATED METHODS

(75) Inventors: Alan McLeod, Somerset (GB); Christopher Reah, Taunton (GB)

(73) Assignee: NuVasive, Inc., San Diego, CA (US)

( * ) Notice: Subject to any disclaimer, the term of this patent is extended or adjusted under 35 U.S.C. 154(b) by 941 days.

(21) Appl. No.: 12/190,974

(22) Filed: Aug. 13, 2008

(65) Prior Publication Data

US 2009/0048677 A1    Feb. 19, 2009

Related U.S. Application Data

(60) Provisional application No. 60/964,627, filed on Aug. 13, 2007.

(51) Int. Cl.
*A61F 2/44* (2006.01)

(52) U.S. Cl. .................................................... 623/17.11

(58) Field of Classification Search ..... 623/17.11–17.16
See application file for complete search history.

(56) References Cited

U.S. PATENT DOCUMENTS

| | | |
|---|---|---|
| 3,867,728 A | 2/1975 | Stubstad et al. |
| 3,875,595 A | 4/1975 | Froning |
| 4,280,954 A | 7/1981 | Yannas et al. |
| 4,309,777 A | 1/1982 | Patil |
| 4,349,921 A | 9/1982 | Kuntz |
| 4,458,678 A | 7/1984 | Yannas et al. |
| 4,512,038 A | 4/1985 | Alexander et al. |
| 4,714,469 A | 12/1987 | Kenna |
| 4,759,766 A | 7/1988 | Buettner-Janz et al. |
| 4,759,769 A | 7/1988 | Hedman et al. |
| 4,772,287 A | 9/1988 | Ray et al. |
| 4,863,476 A | 9/1989 | Shepperd |
| 4,863,477 A | 9/1989 | Monson |
| 4,880,429 A | 11/1989 | Stone |
| 4,904,260 A | 2/1990 | Ray et al. |
| 4,911,718 A | 3/1990 | Lee et al. |
| 4,917,704 A | 4/1990 | Frey et al. |
| 4,932,969 A | 6/1990 | Frey et al. |
| 4,932,975 A | 6/1990 | Main et al. |
| 4,946,378 A | 8/1990 | Hirayama et al. |
| 4,955,908 A | 9/1990 | Frey et al. |
| 5,002,576 A | 3/1991 | Fuhrmann et al. |
| 5,007,934 A | 4/1991 | Stone |
| 5,047,055 A | 9/1991 | Bao et al. |
| 5,108,438 A | 4/1992 | Stone |
| 5,123,926 A | 6/1992 | Pisharodi |
| 5,171,280 A | 12/1992 | Baumgartner |
| 5,171,281 A | 12/1992 | Parsons et al. |

(Continued)

FOREIGN PATENT DOCUMENTS

DE    4315757 C    11/1994

(Continued)

*Primary Examiner* — Nicholas Woodall
(74) *Attorney, Agent, or Firm* — Jonathan Spangler; Heather Prado

(57) ABSTRACT

A prosthesis for the replacement of an intervertebral disc of the spine comprises a block of an elastomeric material, which is held under compression by an encapsulating textile fabric. A preferred version of the invention has flanges that are continuations of the encapsulating fabric forming an interdigitation, with the continuation of the upper fabric passing through a hole in the lower fabric and being attached to the lower vertebral body and the continuation of the lower fabric crossing to its fixation site on the upper vertebral body. Optionally, the flanges are resorbable, over time leaving only the implant core and encapsulation fabric in the intervertebral space.

10 Claims, 13 Drawing Sheets

U.S. PATENT DOCUMENTS

| | | | |
|---|---|---|---|
| 5,192,326 A | 3/1993 | Bao et al. | |
| 5,246,458 A | 9/1993 | Graham | |
| 5,258,043 A | 11/1993 | Stone | |
| 5,306,308 A | 4/1994 | Gross et al. | |
| 5,306,309 A | 4/1994 | Wagner et al. | |
| 5,383,884 A | 1/1995 | Summers | |
| 5,401,269 A | 3/1995 | Buttner-Janz et al. | |
| 5,458,643 A | 10/1995 | Oka et al. | |
| 5,507,816 A | 4/1996 | Bullivant | |
| 5,522,898 A | 6/1996 | Bao | |
| 5,534,023 A | 7/1996 | Henley | |
| 5,534,028 A | 7/1996 | Bao et al. | |
| 5,534,030 A | 7/1996 | Navarro et al. | |
| 5,540,688 A | 7/1996 | Navas | |
| 5,545,229 A | 8/1996 | Parsons et al. | |
| 5,549,679 A | 8/1996 | Kuslich | |
| 5,562,736 A | 10/1996 | Ray et al. | |
| 5,562,738 A | 10/1996 | Boyd et al. | |
| 5,571,189 A | 11/1996 | Kuslich | |
| 5,645,597 A | 7/1997 | Krapiva | |
| 5,674,296 A | 10/1997 | Bryan et al. | |
| 5,676,702 A | 10/1997 | Ratron | |
| 5,683,464 A | 11/1997 | Wagner et al. | |
| 5,683,465 A | 11/1997 | Shinn et al. | |
| 5,702,450 A | 12/1997 | Bisserie | |
| 5,702,454 A | 12/1997 | Baumgartner | |
| 5,705,780 A | 1/1998 | Bao | |
| 5,716,416 A | 2/1998 | Lin | |
| 5,749,916 A | 5/1998 | Richelsoph | |
| 5,755,796 A | 5/1998 | Ibo et al. | |
| 5,976,186 A | 11/1999 | Bao et al. | |
| 5,990,378 A | 11/1999 | Ellis | |
| 6,093,205 A | 7/2000 | McLeod et al. | |
| 6,110,210 A | 8/2000 | Norton et al. | |
| 6,174,330 B1 | 1/2001 | Stinson | |
| 6,187,043 B1 | 2/2001 | Ledergerger | |
| 6,270,530 B1 | 8/2001 | Eldridge et al. | |
| 6,283,998 B1 | 9/2001 | Eaton | |
| 6,371,990 B1 | 4/2002 | Ferree | |
| 6,416,776 B1 | 7/2002 | Shamie | |
| 6,419,704 B1 | 7/2002 | Ferree | |
| 6,428,544 B1 | 8/2002 | Ralph et al. | |
| 6,447,548 B1 | 9/2002 | Ralph et al. | |
| 6,620,196 B1 | 9/2003 | Trieu | |
| 6,712,853 B2 | 3/2004 | Kuslich | |
| 6,746,485 B1 | 6/2004 | Zuchermann et al. | |
| 6,827,743 B2 | 12/2004 | Eisermann et al. | |
| 6,893,466 B2 | 5/2005 | Trieu | |
| 6,955,689 B2 | 10/2005 | Ryan et al. | |
| 7,004,970 B2 | 2/2006 | Cauthen III et al. | |
| 7,018,412 B2 | 3/2006 | Ferreira et al. | |
| 7,066,960 B1 * | 6/2006 | Dickman | 623/17.16 |
| 7,153,325 B2 | 12/2006 | Kim et al. | |
| 7,214,225 B2 | 5/2007 | Ellis et al. | |
| 7,318,840 B2 | 1/2008 | McKay | |
| 7,338,531 B2 | 3/2008 | Ellis et al. | |
| 7,341,601 B2 | 3/2008 | Eisermann et al. | |
| 7,445,634 B2 | 11/2008 | Trieu | |
| 7,588,574 B2 | 9/2009 | Assell et al. | |
| 7,604,653 B2 | 10/2009 | Kitchen | |
| 7,618,457 B2 | 11/2009 | Hudgins | |
| 7,682,400 B2 | 3/2010 | Zwirkoski | |
| 7,758,647 B2 | 7/2010 | Arnin et al. | |
| 7,887,593 B2 | 2/2011 | McKay et al. | |
| 7,905,922 B2 | 3/2011 | Bergeron | |
| 7,959,683 B2 | 6/2011 | Semler et al. | |
| 2002/0026244 A1 | 2/2002 | Trieu | |
| 2002/0058947 A1 | 5/2002 | Hochschuler et al. | |
| 2002/0077701 A1 | 6/2002 | Kuslich | |
| 2002/0077702 A1 | 6/2002 | Castro | |
| 2002/0123750 A1 | 9/2002 | Eisermann et al. | |
| 2003/0129257 A1 | 7/2003 | Nies et al. | |
| 2003/0220691 A1 | 11/2003 | Songer et al. | |
| 2004/0113801 A1 | 6/2004 | Gustafson et al. | |
| 2004/0243237 A1 | 12/2004 | Unwin et al. | |
| 2005/0015140 A1 | 1/2005 | deBeer | |
| 2005/0027364 A1 | 2/2005 | Kim et al. | |
| 2005/0055094 A1 | 3/2005 | Kuslich | |
| 2005/0119725 A1 | 6/2005 | Wang et al. | |
| 2005/0177240 A1 | 8/2005 | Blain | |
| 2005/0192669 A1 | 9/2005 | Zdeblick et al. | |
| 2005/0228500 A1 | 10/2005 | Kim et al. | |
| 2006/0085080 A1 | 4/2006 | Bechgaard et al. | |
| 2006/0116774 A1 | 6/2006 | Jones et al. | |
| 2006/0200137 A1 | 9/2006 | Soboleski et al. | |
| 2006/0293662 A1 | 12/2006 | Boyer, II et al. | |
| 2007/0055373 A1 | 3/2007 | Hudgins et al. | |
| 2007/0100453 A1 | 5/2007 | Parsons et al. | |
| 2007/0112428 A1 | 5/2007 | Lancial | |
| 2008/0228273 A1 | 9/2008 | McLeod et al. | |
| 2008/0269900 A1 | 10/2008 | Reah et al. | |
| 2008/0306593 A1 | 12/2008 | McLeod et al. | |
| 2008/0306595 A1 | 12/2008 | McLeod et al. | |
| 2009/0105826 A1 | 4/2009 | McLeod et al. | |
| 2010/0286778 A1 | 11/2010 | Eisermann et al. | |
| 2010/0320639 A1 | 12/2010 | Reah et al. | |
| 2011/0060366 A1 | 3/2011 | Heim et al. | |

FOREIGN PATENT DOCUMENTS

| | | |
|---|---|---|
| EP | 0346129 A1 | 12/1989 |
| EP | 0346269 A2 | 12/1989 |
| EP | 0453393 A1 | 10/1991 |
| EP | 0179695 B1 | 12/1991 |
| EP | 0599419 A2 | 6/1994 |
| EP | 0621020 A1 | 10/1994 |
| EP | 0662309 A1 | 7/1995 |
| EP | 0563332 B1 | 8/1995 |
| EP | 0747025 A1 | 12/1996 |
| EP | 0820740 A1 | 1/1998 |
| EP | 0744162 B1 | 2/2003 |
| EP | 1318167 A2 | 6/2003 |
| WO | WO 91/00713 A1 | 1/1991 |
| WO | WO 92/10982 A1 | 7/1992 |
| WO | WO 93/16664 A1 | 9/1993 |
| WO | WO 95/19153 A1 | 7/1995 |
| WO | WO 95/25487 A1 | 9/1995 |
| WO | WO 95/31946 A1 | 11/1995 |
| WO | WO 96/11639 A1 | 4/1996 |
| WO | WO 96/11642 A1 | 4/1996 |
| WO | WO 96/40014 A1 | 12/1996 |
| WO | WO 97/20526 A1 | 6/1997 |
| WO | WO 98/22050 A1 | 5/1998 |
| WO | WO 01/21246 A1 | 3/2001 |
| WO | WO 02/11650 A2 | 2/2002 |
| WO | WO 03/068111 A1 | 8/2003 |
| WO | WO 03/077806 A1 | 9/2003 |
| WO | WO 2004/002374 A1 | 1/2004 |
| WO | WO 2005/004941 A1 | 1/2005 |
| WO | WO 2005/092211 A1 | 10/2005 |
| WO | WO 2005/092247 A1 | 10/2005 |
| WO | WO 2005/092248 A1 | 10/2005 |
| WO | WO 2005/112833 A1 | 12/2005 |
| WO | WO 2006/133130 A2 | 12/2006 |
| WO | WO 2007/012070 A2 | 1/2007 |
| WO | WO 2007/020449 A2 | 2/2007 |
| WO | WO 2007/067547 A2 | 6/2007 |
| WO | WO 2008/098125 A2 | 8/2008 |
| WO | WO 2008/131310 A1 | 10/2008 |
| WO | WO 2009/006455 A1 | 1/2009 |

* cited by examiner

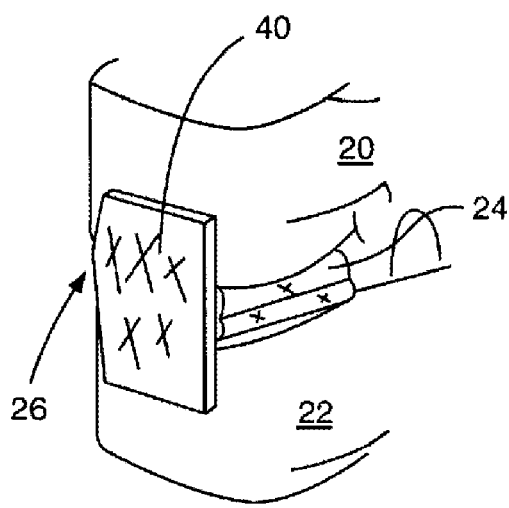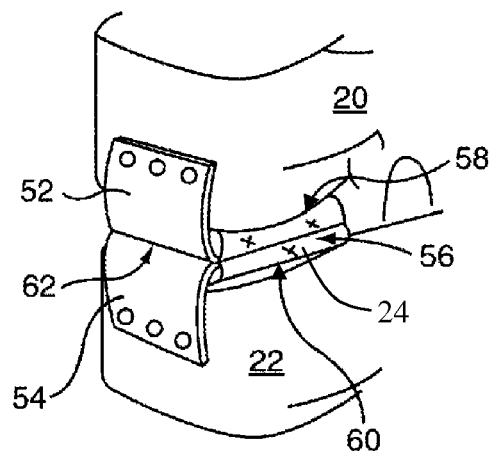
FIG. 6          FIG. 7
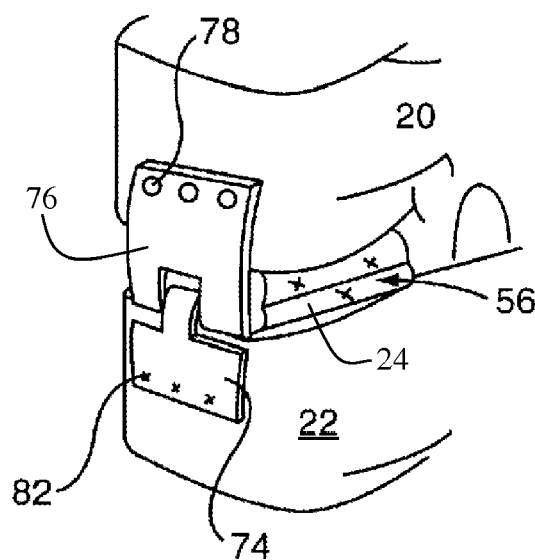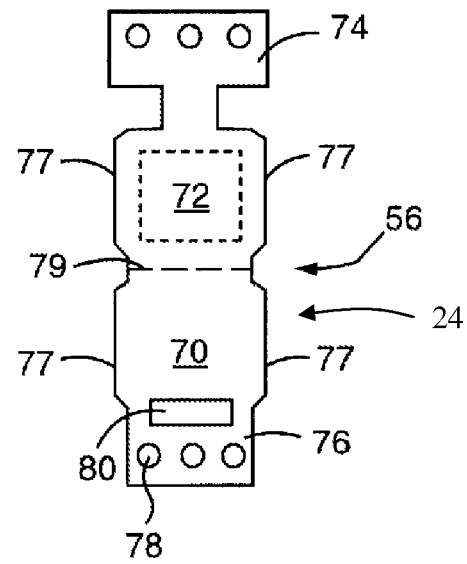
FIG. 8          FIG. 9

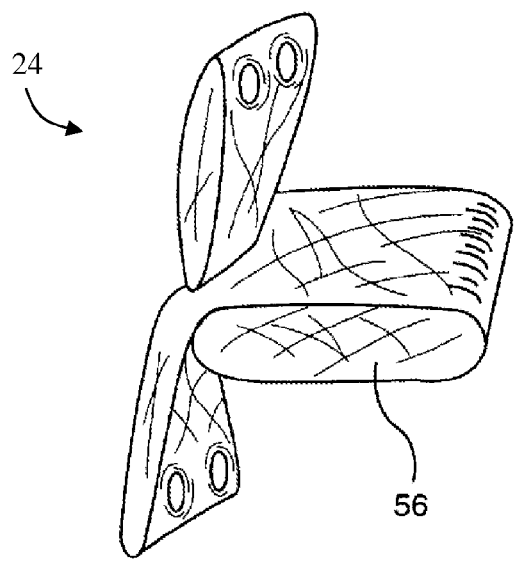
FIG. 10
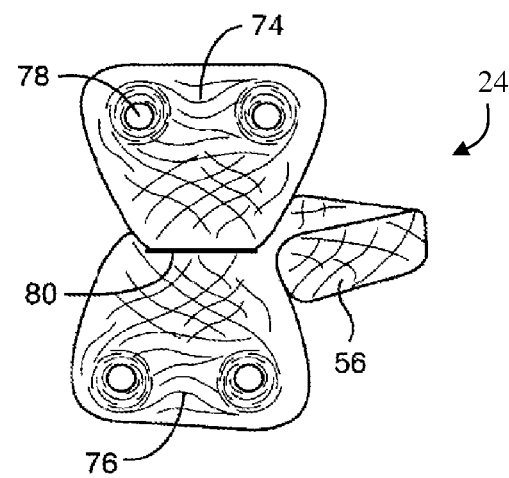
FIG. 11
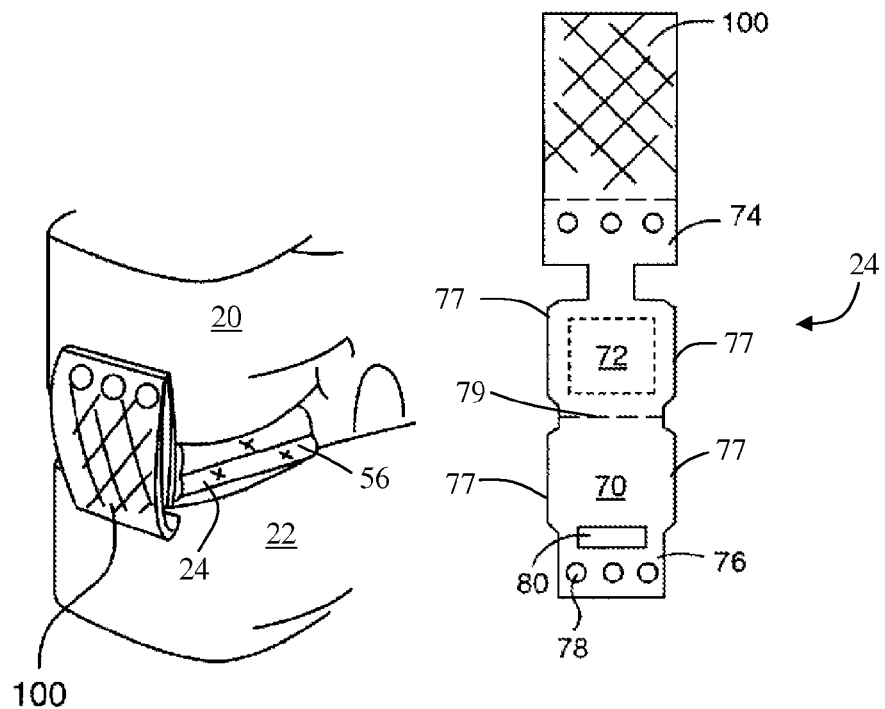
FIG. 12
FIG. 13

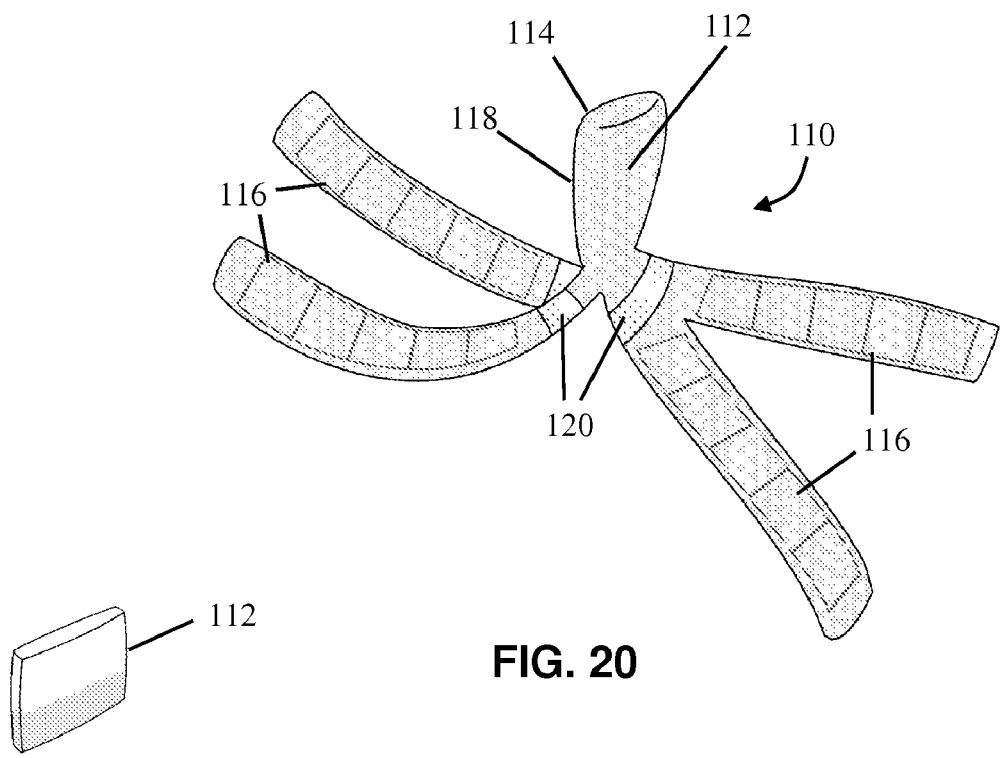
FIG. 20
FIG. 20a
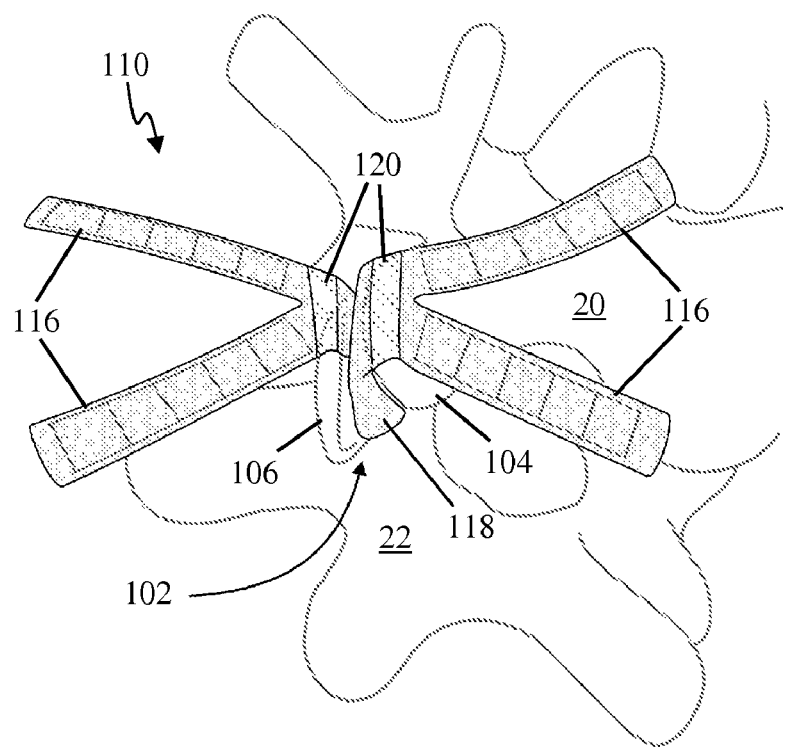
FIG. 21

BIORESORBABLE SPINAL IMPLANT AND RELATED METHODS

CROSS REFERENCES TO RELATED APPLICATIONS

The present application is a nonprovisional patent application claiming benefit under 35 U.S.C. §119(e) from U.S. Provisional Application Ser. No. 60/964,627, filed on Aug. 13, 2007, the entire contents of which are hereby expressly incorporated by reference into this disclosure as if set forth fully herein. The present application also incorporates by reference the following commonly owned publications in their entireties: PCT Application No. PCT/US2008/060944 entitled "Textile-Based Surgical Implant and Related Methods," filed Apr. 18, 2008; PCT Application Serial No. PCT/US2008/068868, entitled "Facet Joint Implant and Related Methods," filed Jun. 30, 2008; and U.S. Pat. No. 6,093,205, entitled "Surgical Implant," issued Jul. 25, 2000.

BACKGROUND OF THE INVENTION

I. Field of the Invention

The present invention relates generally to a surgical implant and, more particularly, to an embroidered implant with resorbable flanges.

II. Discussion of the Prior Art

Various forms of disc replacement are in use, although historically the favored treatment particularly for a failed cervical disc has been disectomy followed by fusion, using a block or plug of bone inserted into the front of the disc space and abutting into the vertebrae above and below. This bone graft may or may not be stabilized using a plate fastened across the front of the disc space. Although fusion may relieve the symptoms for which the surgery was indicated, the loss in mobility of the particular spinal segment is undesirable, particularly in the cervical spine. The fusion of the disc segment also results in hypermobility of the motion segments above and below the fusion with increased strain on the adjacent discs, which can result in their accelerated degeneration, which will in turn require surgical intervention. Fusion using bone graft will have associated donor site morbidity if the bone is autograft or associated risks of infection if the bone is allograft. Alternatively, following the disectomy the disc space may be left empty, but this may lead to hypermobility problems at the operative level, kyphosis, spontaneous fusion and a loss in foraminal height.

Disc prostheses based on either articulating metal plates or metal end plates supporting a polyethylene spacer are in clinical use. Articulating devices reduce the loss in spinal mobility and the degeneration of adjacent discs. However, optimal positioning of the articulating disc prosthesis can sometimes prove challenging. The articulation also tends to be non-viscoelastic, with a fixed axis of rotation and can be under-constrained in axial rotation and distraction such that it does not truly emulate normal motion. As well as the general geometry mismatch, such prosthesis can also be adversely affected by the ingrowth of scar tissue.

The present invention is directed at overcoming, or at least improving upon, the disadvantages of the prior art.

SUMMARY OF THE INVENTION

The present invention accomplishes this goal by providing an artificial disc that attempts to recreate the physiological movements of the spine and also to provide a manner of securing the artificial disc in situ immediately, post-operatively and long term by using bioresorbable fabric that initially encloses, holds, and securely fastens the implant in place to adjacent vertebrae. Over time, the fabric portion that secures the implant to adjacent vertebrae, may resorb, thus leaving only the encapsulation fabric containing the implant core within the intervertebral space.

According to a first aspect of the invention, a prosthesis is provided having a core element provided in a retaining fabric. An example of a suitable embroidered implant is shown and described in commonly owned U.S. Pat. No. 6,093,205, the entire contents of which are hereby incorporated by reference into this disclosure as if set forth fully herein. The terms "block," "core," "spacer," and "insert" are used in an interchangeable manner in this document. The fabric is designed to constrain the element. The fabric may be discontinuous, for instance having apertures or gaps in the fabric. The fabric may engage two or more opposing faces and/or two or more opposing edges and/or two or more opposing corners of the element to restrain it. Engagement with the rear, front, and side faces is preferred. Ideally, engagement with the top and bottom face may also be provided. Full enclosure of the element by the fabric represents a preferred form of the invention.

According to a second aspect of the invention, the disc prosthesis comprises a block of an elastomeric or viscoelastic material which is encapsulated by a textile fabric. The block could equally well be referred to as a core or insert provided within the textile fabric of the prosthesis. Preferably, the block is formed of silicon rubber, however other materials are possible, including but not limited to elastomers, hydrogel, hydrogel beads, plastic mesh, plastic constructs, injectable fluids, curable fluids, hair and hair constructs encapsulated in fabric. Preferably, the block has a Shore A scale hardness of 35 to 80 degrees. The block is preferably formed of a biocompatible material. The block may be formed of a reabsorbable material. Preferably the block provides substantially equivalent properties and/or behavior to the nucleus pulposis of a natural disc, for instance during compression, distraction, horizontal gliding, axial rotation, flexion, and/or extension.

According to an alternative embodiment of the second aspect of the invention, the disc prosthesis comprises a textile spacer encapsulated by a textile fabric jacket. An example of a suitable implant having a textile core is shown and described in commonly owned PCT Application No. PCT/US2008/060944 entitled "Textile-Based Surgical Implant and Related Methods," the entire contents of which are hereby incorporated by reference into this disclosure as if set forth fully herein. The textile/fabric spacer may be constructed from any of a variety of natural or synthetic fibrous materials, for example including but not limited to polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, nylon, silk, cellulosic and polycaprolactone fibers. The spacer may be manufactured via any number of textile processing techniques (e.g. embroidery, weaving, three-dimensional weaving, knitting, three-dimensional knitting, injection molding, compression molding, cutting woven or knitted fabrics, etc.). For the purposes of this disclosure, "textile" is meant to include any fibrous material (including but not limited to those delineated above) processed by any textile processing technique (including but not limited to those delineated above).

The block may be provided with a flat upper surface and/or a flat lower surface. The block may be provided with upper and/or lower surfaces that are curved in a convex manner. The maximum thickness of such blocks may be centrally provided. The provision of both planar upper and/or lower surfaces is preferred. The area of the upper surface is preferably greater than the area of the lower surface. The maximum width of the upper surface is preferably greater than the maximum width of the lower surface. The minimum width of the upper surface is preferably greater than the minimum width of the lower surface. The block may be provided with sides extending between the upper and lower surfaces. The sides may be planar or curved, most preferably curved in a convex manner.

Although the front thickness of the block may be less than the back thickness of the block, preferably the front thickness of the block is more than the back thickness of the block. The "front" as used herein refers to the portion of the block nearer the front of the spine in use. The thickness of the front and back of the block may be equal and less than the thickness at a point partway, for instance midway, between the front and the back of the block. The block may be wider towards the rear face than towards the front face, but the block is preferably wider towards the front face than towards the rear face. The width may decrease in a linear manner from in proximity to the front face to in proximity to the rear face of the block.

The interface between the sides and top and/or bottom surfaces may be curved. The interface between the sides and front and/or rear faces of the block may be curved. Likewise, the interface between the front and/or rear face and the top and/or bottom faces may be curved.

Preferably the maximum length (l) from the front face of the block to the rear face of the block is between 8 and 18 mm and more preferably between 10 and 15 mm. Preferably the maximum width of the upper surface is between 10 and 18 mm, and more preferably between 12.5 and 16.5 mm. Preferably the minimum upper width is between 8 and 15 mm and more preferably between 9.5 and 13.5 mm. Preferably the maximum lower width is between 9 and 16 mm, and more preferably between 10.5 and 14.5 mm. Preferably the minimum lower width is between 7.5 and 13.5 mm and more preferably between 8.5 and 12.5 mm. Preferably the maximum thickness of the block is between 2 and 6 mm, and more preferably between 2.5 and 5.5 mm. Preferably the minimum thickness of the block is between 1.25 and 4.75 mm and more preferably between 1.75 and 4.25 mm.

A particularly preferred form of the block provides planar upper and lower surfaces, the upper surface having a greater width than the lower surface, the block having a greater thickness towards the front face than towards the rear face. The front face may be planar and/or the rear face may be curved.

In one embodiment of the invention, the encapsulated disc prosthesis is preferably a rectangular block (although it may have a circular or oval cross-section). Typical dimensions for a disc prosthesis for the cervical spine would be 13 mm wide by 12 mm deep by 4 mm in height.

The encapsulating jacket may be constructed from any of a variety of natural or synthetic fibrous materials, for example including but not limited to polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, nylon, silk, cellulosic and polycaprolactone fibers. The jacket may be manufactured via any number of textile processing techniques (e.g. embroidery, weaving, three-dimensional weaving, knitting, three-dimensional knitting, injection molding, compression molding, cutting woven or knitted fabrics, etc.). The fabric may be produced in the desired profile or may be reduced to the desired profile from a larger amount of fabric, for instance by cutting or pressing. The structure and/or properties of the fabric may be selected to encourage tissue ingrowth, such as providing a encapsulating jacket that is sufficiently porous to allow for tissue and/or bony ingrowth.

The materials selected to form the spacer and/or jacket may be specifically selected depending upon the target location/use within the body (e.g. spinal, general orthopedic, and/or general surgical). For example in many instances it may be preferable to select UHMWPe fibers in order to generate a specific tissue response, such as limited tissue and/or bony ingrowth. In some instances it may be desirable to modify the specific fibers used, such as providing a surface modification to change or enhance a desired tissue response.

The jacket may encapsulate the spacer fully (i.e. disposed about all surfaces of the spacer) or partially (i.e. with one or more apertures formed in the jacket allowing direct access to the spacer). The various layers and/or components of the spacer may be attached or unattached to the encapsulating jacket. The jacket may optionally include one or more fixation elements for retaining the jacket in position after implantation, including but to limited to at least one flange extending from or otherwise coupled to the jacket and screws or other affixation elements (e.g. nails, staples, sutures, adhesives, tacks, etc.) to secure the flange to an adjacent anatomical structure (e.g. vertebral body). This may be facilitated by providing one or more apertures within the flange(s) dimensioned to receive the screws or other fixation elements.

The fabric component may be formed from a planar fabric element. The fabric component may be formed from a piece of fabric having a first portion and a second portion, the first and second portions being joined by an integral part of the fabric or by an attaching technique, such as stitching. Preferably the first and second portions are folded, or otherwise provided in opposition to one another, to give the block encapsulating portion of the fabric component. The edges of the first and second portions may be stitched or otherwise attached to one another to provide the encapsulating portion of the fabric component. A pocket, open at one end, may be formed in this way.

The fabric component may be provided with one or more further portions, preferably attached to the first and/or second portion, to provide closure for the pocket receiving the block. A single further portion, extending across the opening may be provided. Alternatively, a first further portion attached to the first portion and a second further portion attached to the second portion may be provided, the first and second further portions being attached to one another to provide closure for the pocket.

The first and second further portions may extend from the first and second portions, for instance to form flanges. These further portions/flanges may be attached to the vertebrae adjacent to the prosthesis in use. In such cases the first further portion may be attached to the vertebrae adjacent the first portion of the encapsulating material and the second further portion may, additionally or alternatively, be attached to the vertebrae adjacent the second portion of the encapsulating material. Optionally, the first and/or second further portion comprising one or more flanges may be comprised of any suitable strong and flexible material that can bioresorb, biodegrade, bioerode, or bioabsorb. As a further option, any or all of the encapsulating fabric may be bioresorbable, however it is preferable for only the flange portions to be resorbable over time.

In a preferred embodiment of the invention, one of the first or second further portions is provided with an aperture. The other further portion may be provided with a reduced dimension neck in such instances. Preferably the first and second further portions are interdigitated in the assembled form. Interdigitation may be affected by passing one of the further portions through the aperture in the other further portion. The first further portion may be attached to the vertebrae adjacent the second portion of the encapsulating material and/or the second further portion may be attached to the vertebrae adjacent the first portion of the encapsulating fabric.

The gap between the vertebrae may be spanned by a separate fabric element from the prosthesis and attached to the vertebrae adjacent the prosthesis. This element may provide closure of the prosthesis. In an alternative form the element may be provided as a continuation of the first or second further portions of the prosthesis fabric material.

The first and/or second further portions and/or the separate element may be provided with apertures to receive anchors. Anchors such as bone screws, staples or the like may be employed.

In a particularly preferred form of the invention, a portion of one of the further portions passes through an aperture or gap in the other further portion, and an element is provided within the pocket between the block and the location where the one further portion passes through the other. The element is preferably a pad or cushion of resilient but deformable material, for instance the fabric used for the encapsulating fabric. The element may be discrete from the encapsulating fabric. It is preferred, however, that the element be formed of the fabric material and that it be integral with the encapsulating fabric material. The element may be formed by folding a portion of the fabric material. Multiple folds may be used to form the element. The fabric forming the element may be provided on one or both of the further portions and/or on one or both of the portions of the fabric material and/or at the junction between a portion and its further portion. Preferably the block is constrained and/or retained by the fabric, but is not attached to the fabric.

Encapsulation may be provided by fully enclosing the block within the fabric. Encapsulation may be provided by providing the block within a fabric constraint. The fabric constraint, may for instance, engage some or all of the corners and/or some or all of the edges of the block, but be absent from one or more portions of the faces. The encapsulation of the elastomeric block may be by insertion of a solid block or injection of a liquid into a textile receptacle. The textile receptacle may be formed by stitching or sealing closed the ends of a tubular fabric or by folding a fabric onto itself and stitching or sealing closed the free edges. Preferably the fabric compresses the block.

Preferably one or more prostheses as herein defined provide a complete disc replacement, most preferably in the cervical portion of the spine.

Preferably a single disc prosthesis, comprising for instance an elastomeric block held under compression by an encapsulating textile fabric, is inserted into the disc space from the anterior aspect of the spine. Alternatively, a pair of disc prostheses may be inserted into the disc space from the posterior aspect of the spine. Still further alternatively, one or more disc prostheses may be inserted into the disc space from one or more lateral aspects of the spine. Preferably the prosthesis is inserted between two adjacent vertebrae, with the front edge of the textile fabric being level with the front edge of the vertebrae and the elastomeric block recessed relative to the front edge of the vertebrae. Recessing of the block by between 1 and 4 mm is preferred.

Preferably the block component of the prosthesis acts as a replacement for the nucleus pulposis. The encapsulation fabric provides a replacement for the annulus, and optionally, the flange elements provide a replacement for the anterior longitudinal ligament which is the ligament extending along that portion of the spine. Over time, the bioresorbable fabric forming one or more flanges may be absorbed into the vertebrae, leaving only the core element.

According to a third aspect of the invention, a method of producing a disc prosthesis is provided, the method comprising providing a block of an elastomeric or visco-elastic material and forming an encapsulating bioresorbable textile fabric component, the block being placed within the fabric component.

According to a fourth aspect of the invention we provide a set of two or more prosthesis according to the first aspect of the invention and incorporating blocks of different sizes.

According to a fifth aspect of the invention we provide a surgical technique for providing a disc prosthesis, the technique comprising removing the natural disc and replacing the disc with a prosthesis according to the first aspect of the invention.

The third, fourth and fifth aspects of the invention may include any of the details, options and possibilities set out elsewhere in the application.

The present invention is aimed at eliminating or at least reducing the challenges associated with retaining an implant within an intervertebral space so that the implant is post-operatively secure, while using a bioresorbable fabric for the flanges that degrades, erodes, resorbs or absorbs over time and thus allows for increased mobility.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 3a illustrates a top plan view of a block for use in a spinal prosthesis;

FIG. 3b illustrates a maximum cross section of the block of FIG. 3a;

FIG. 3c illustrates a minimum cross section of the block of FIG. 3a;

FIG. 3d illustrates a side view of the block of FIG. 3a;

FIG. 3e illustrates a side view of an alternative embodiment of the block of FIG. 3a;

FIG. 6 is a similar view to FIG. 4 for a further embodiment of the invention but with the "cat's cradle" replaced with a textile fabric which may be either a separate textile fabric placed across the opening of the disc space or a textile fabric that is attached to the disc prosthesis;

FIG. 7 is a similar view to FIG. 6 for a further embodiment of the invention but with the flange element across the front of the disc space created from a continuation of the encapsulating fabric;

FIG. 8 is a similar view to FIG. 7 for a further embodiment of the invention but with the continuation of the encapsulating fabric forming an interdigitation with the continuation of the upper fabric passing through a hole in the lower fabric and being attached to the lower vertebral body and the continuation of the lower fabric crossing to its fixation site on the upper vertebral body;

FIG. 9 is a plan view of the fabric profile used in the FIG. 8 embodiment of the invention;

FIGS. 10 and 11 are perspective views of a modified version of the embodiment of the invention illustrated in FIG. 8;

FIG. 12 is a similar view to FIG. 6 for a further embodiment of the invention but with additional fabric across the front of the device which may either be a separate fabric or a continuation of the encapsulating fabric;

FIG. 13 is a plan view of the fabric profile used in the FIG. 12 embodiment of the invention;

FIG. 20 illustrates an example of an implant for insertion into a facet joint, the implant having biodegradable fabric portions according to one embodiment of the present invention;

FIG. 20a illustrates a core forming part of the implant of FIG. 20;

FIG. 21 illustrates the implant of FIG. 20 positioned after insertion;

DESCRIPTION OF THE PREFERRED EMBODIMENT

Figure 1:
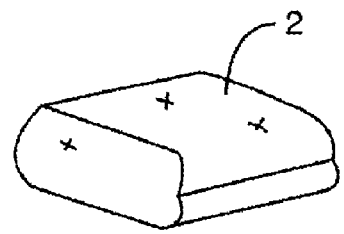
FIG. 1 is a view of the basic prosthetic disc with a textile fabric encapsulating a block of viscoelastic rubber.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The embroidered implant with bioresorbable flanges disclosed herein boasts a variety of inventive features and components that warrant patent protection, both individually and in combination.

A variety of embodiments may be used to construct the implant of the present invention. Generally, the implant disclosed herein comprises a core provided with or without an encapsulating jacket. Examples of specific embodiments of the implant are described in detail below. The implant disclosed herein is suitable for use in a variety of surgical applications, including but not limited to spine surgery. The compliant nature of the implant provides the required flexibility and elasticity to advantageously support the full range of physiological movements, as opposed to fusion surgery which forms a boney bridge between adjacent articular processes. In addition, the porosity and biocompatibility of the implant may facilitate tissue and/or bony ingrowth throughout part or all of the implant (if desired), which helps to secure and encapsulate the implant in a facet joint.

A variety of materials can be used to form the core and/or encapsulating jacket of the implant. The core is preferably formed of biocompatible material. In one embodiment, the core is formed of a textile/fabric material throughout, similar to that shown and described in the above-referenced '944 PCT Application. The textile/fabric core may be constructed from any of a variety of natural or synthetic fibrous materials, for example including but not limited to polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, nylon, silk, cellulosic and polycaprolactone fibers. The core may be manufactured via any number of textile processing techniques (e.g. embroidery, weaving, three-dimensional weaving, knitting, three-dimensional knitting, injection molding, compression molding, cutting woven or knitted fabrics, etc.). For the purposes of this disclosure, "textile" is meant to include any fibrous material (including but not limited to those delineated above) processed by any textile processing technique (including but not limited to those delineated above). In another embodiment, the core comprises at least one of an elastomer (e.g. silicon), hydrogel, hydrogel beads, plastic mesh, plastic constructs, injectable fluids, curable fluids, hair and hair constructs encapsulated in fabric, similar to that shown and described in the above-referenced '205 patent.

The encapsulating jacket may be constructed from any of a variety of natural or synthetic fibrous materials, for example including but not limited to polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, nylon, silk, cellulosic and polycaprolactone fibers. The jacket may be manufactured via any number of textile processing techniques (e.g. embroidery, weaving, three-dimensional weaving, knitting, three-dimensional knitting, injection molding, compression molding, cutting woven or knitted fabrics, etc.). The jacket may encapsulate the core fully (i.e. disposed about all surfaces of the core) or partially (i.e. with one or more apertures formed in the jacket allowing direct access to the core). The various layers and/or components of the core may be attached or unattached to the encapsulating jacket. The jacket may optionally include one or more fixation elements for retaining the jacket in position after implantation, including but to limited to at least one flange extending from or otherwise coupled to the jacket and screws or other affixation elements (e.g. nails, staples, sutures, adhesives, tacks, etc.) to secure the flange to an adjacent anatomical structure (e.g. vertebral body). This may be facilitated by providing one or more apertures within the flange(s) dimensioned to receive the screws or other fixation elements.

In FIG. 1, a core comprising an elastomeric block is encapsulated and held in compression by a textile fabric jacket 2. The elastomeric block may be a silicone rubber, for instance with a Shore A scale hardness of 35-80 degrees. The structure of the fabric (e.g. porosity) is selected such that fibrous tissue may penetrate between the fibers or threads forming the fabric. Tissue and/or bony ingrowth is highly desirable and may even be possible to an extent where ingrowth replaces one or more components of the prosthesis. Biodegradation, bioresorbtion, bioabsorbtion, bioabsorption, and/or bioerosion of the prosthesis or portions thereof may be encouraged in such cases, for instance giving rise to replacement of the fabric and/or even disc regrowth. For the purposes of this disclosure, bioresorbtion is meant to include any biological process (including those delineated above) in which at least a portion of the fabric component of the implant disappears or becomes detached from the rest of the implant.

Figure 2:
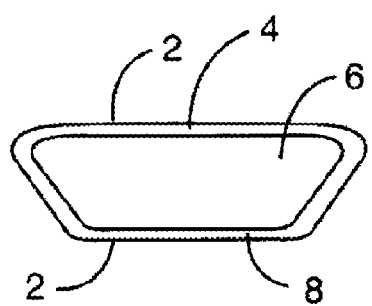
FIG. 2 is a view of the preferred cross-section in the frontal plane for a cervical disc.

In FIG. 2, the cross section has been modified to match that of the natural cervical disc with the upper surface 4 of the disc 6 having a larger surface area than the lower surface 8 of the disc. The textile fabric 2 conforms to the profile of the disc 6. To render the prosthesis suitable for use in replacing the different discs of the spine (with their consequential variation in size) and to render the prosthesis suitable for treating a variety of patient sizes (with consequential variation in the size of the discs to be replaced) the core for the prosthesis is provided in a variety of sizes.

Figures 3A, 3B, 3C:
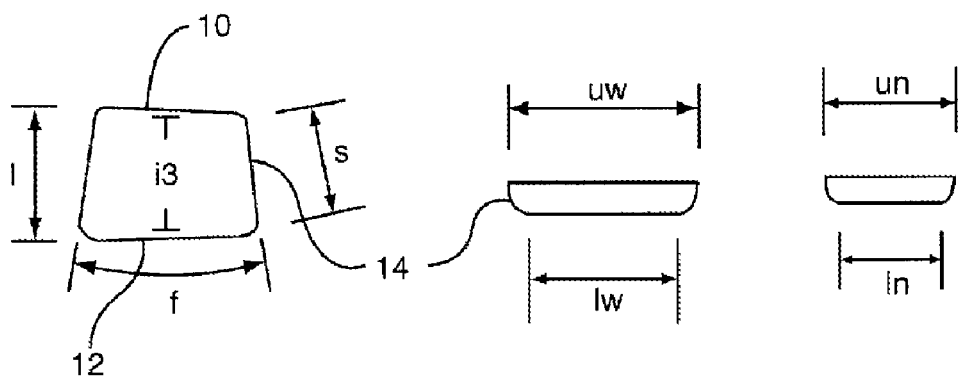

As illustrated in FIGS. 3a, 3b, 3c and 3d, a variety of dimensions are of relevance in detailing the size of prosthesis core provided. In FIG. 3a the maximum length, l, from the front face 10 of the disc to the rear face 12 of the disc is illustrated, together with the actual length, s, of the inclined side 14 connecting the front face 10 of the core to the junction with the rear face 12 of the core. The length f of the rear face 12 is also illustrated.

FIG. 3b illustrates the maximum cross section of the core, normally taken parallel to front face 10, and generally the cross section extending between one rear face 12 to side 14 junction and the other rear face 12 to side 14 junction. The cross section also illustrates the maximum upper width, uw, and the maximum lower width, lw.

FIG. 3c displays the minimum width cross section, generally provided at or in proximity to the front face 10. This Figure illustrates the minimal upper width, un, and the lower minimal width, ln.

Figure 3D:
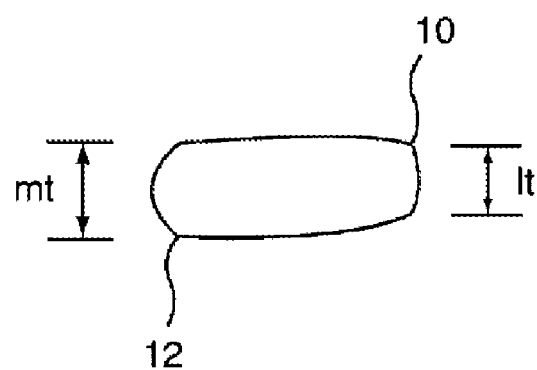
Figure 3E:

FIG. 3d illustrates, from the side, the variation in thickness of the core between the front face 10 and the rear face 12. The maximum thickness, mt, is generally provided at or in proximity to the rear face 12, with the lowest thickness, lt, generally being provided at or in proximity to the front face 10. The corners of the core are generally rounded, as illustrated.

Sets of prostheses of different sizes may be offered for a particular disc in the spine. The correct size may be evaluated by inserting into the vacant disc space metal sizers, each provided on a rod, and of each corresponding in its dimensions to the profile of a prosthesis.

Figure 4:
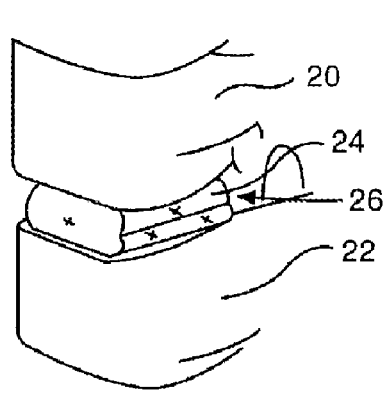
FIG. 4 is a view of the basic prosthetic disc in situ between adjacent spinal vertebrae.

FIG. 4 is a perspective view of the prosthetic disc 24 inserted in the intervertebral space 26 between adjacent vertebral bodies 20, 22. Prostheses of the type provided by example in the present invention are typically inserted following a disectomy. This involves removing a portion of the anterior longitudinal ligament spanning the vertebral space at issue, removing the disc (both annulus and nucleus pulposis) and inserting the prosthesis into the vacant disc space. Where applicable, the prosthesis is then anchored in place, as described below in more detail. The front edge of the solid core is positioned level with, or more preferably recessed relative to the front edge of the vertebrae, for instance by 2 to 4 mm.

This technique is surgically attractive in that the preparation of the disc space, to receive the disc prosthesis, involves steps already established for standard disc removal surgery. The surgeon is thus not required to change techniques.

Figure 5:
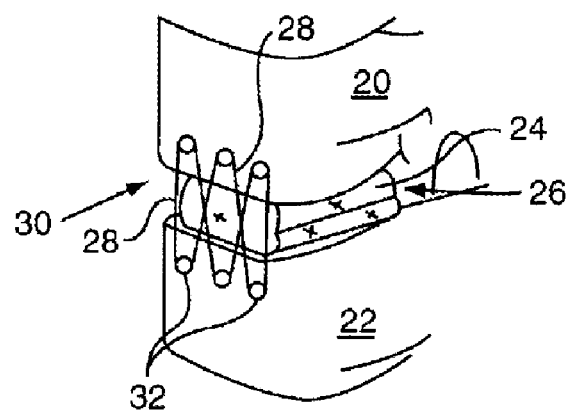
FIG. 5 is a similar view to FIG. 4 for a further embodiment of the invention with the addition of a "cat's cradle" of suture threads.

As shown in FIG. 5, a "cat's cradle" construction 28 may be added to the front 30 of the spine to provide security to the implant 24. The cradle construction 28 is anchored to the vertebral bodies 20, 22 on either side of the intervertebral space 26 using fixation devices 32 imbedded into the vertebrae and defining the apex of each element of the cradle. Alternatively the cradle construction 28 may be formed by passing the elements of the cradle, for example a suture, around the head of a screw secured to the vertebral body to define the apex of each cradle element. Other fixings, such as staples, may be used in this and other embodiments of the present invention.

This construction 28 may be formed of either single or multiple yarns, sutures, braids or other flexible textile elements which are formed into a loop either before or during the operation. Any of the single or multiple yarns, sutures, braids or other flexible textile elements may be made of bioresorbable material such that over time only the core element of the implant remains between the adjacent vertebral bodies.

The cradle construction 28 acts to secure the prosthetic disc 24 within the intervertebral space 26 while the spine is being flexed, extended or rotated. The cradle construction 28 also acts to support the motion segment of the spine by providing textile fibres that match the orientation of the fibres within the anterior portion of the natural annulus, which is the fibrous structure across the front of the disc space. The cradle construction 28 may be added to any of the embodiments of the spinal implant of the present invention shown by way of example in FIGS. 6, 7, 8, and/or 12.

FIG. 6 shows one example of an alternate embodiment of the prosthetic disc 24 of the present invention in which the cradle is replaced with a preformed fabric element 40, which may have fibers arranged within it which match the orientation of the cradle structure detailed above. This fabric element 40 may be either a separate element positioned across the front of the disc space 26 after the insertion of the prosthetic disc 24, as shown, or it may be attached to the disc 24. The element 40 may be secured to the vertebral bodies 20, 22 on either side of the disc space 26 by sutures passing to bone anchors (not shown) implanted into the vertebrae. Alternatively, the fabric element 40 may be secured using bone screws passing either directly through the fabric element 40 or inserted through fixation holes in the fabric, with or without the use of a reinforcing element, such as a washer or rivet. Alternatively the fabric element 40 may be secured by a pair of metal plates, one of which is fastened to each vertebral body 20, 22 over the fabric element 40. The fabric element 40 may be formed of a bioresorbable fabric such that it is absorbed by the body over time.

FIG. 7 illustrates another example of a prosthetic disc 24 according to the present invention, in which the fabric forming the flanges 52, 54, each for attachment to vertebral bodies 20, 22, is a continuation of the encapsulating fabric 56. The fabric 56 on the upper surface 58 of the prosthetic disc passes to the front of the upper vertebral body 20 and the fabric 56 on the lower surface 60 of the prosthetic disc passes to the front of the lower vertebral body 22. The elastomeric block within the fabric 56 is held in position by the upper and lower flanges 52, 54 being fastened to each other in a line 62 along the front edge of the prosthetic disc.

FIGS. 8-9 show another example of a prosthetic disc 24 according to the present invention. FIG. 8 illustrates the implant inserted between adjacent vertebral bodies 20, 22. FIG. 9 illustrates a plan profile of the encapsulating textile fabric 56 of the implant shown in FIG. 8 before the sides of the encapsulating fabric 56 have been fastened together. The view shows the inside surfaces of the lower face 70 and upper face 72 of the encapsulating fabric 56, the faces 70, 72 facing one another in the assembled form, the core (not shown) being provided between these two faces. The continuations or flanges 74, 76 of the encapsulating fabric 56 form an interdigitation in the assembled state.

To assemble the encapsulating fabric 56, faces 70, 72 are sewn together along edges 77 to form a pocket sealed at the edges 77 by the stitches and at the back by the junction 79 of the two faces 70, 72. The continuation/flange 74 of the upper fabric 72 is passed through a hole 80 in the continuation/flange of the lower fabric 76 and is attached to the lower vertebral body 22. The continuation/flange 76 of the lower fabric crosses over to its fixation site on the upper vertebral body 20 as a result.

For the purposes of illustration by way of example only, the flange 76 attached to the upper vertebral body 20 is secured using bone screws (not shown) received in apertures 78 in the flange 76 and the flange 74 attached to the lower vertebral body 22 is attached using sutures 82 which are in turn attached to bone anchors (not shown) imbedded in the vertebral body underneath the flange 74.

The tension on the flanges 74, 76 created by the extension of the spine will tend to pull the disc element even more securely back within the disc space. This is contrary to some prior art prostheses in which particularly extension of the spine can tend to promote the ejection of the disc element out of the disc space.

The visco-elastic properties of the prosthetic disc are an ideal match of the visco-elastic properties of the natural disc when the encapsulated textile/elastomeric inserts are subjected to compression/relaxation with the constructs illustrated in FIGS. 8 and 9. Flexion of the spine will impose a direct compressive load on the prosthetic disc and extension of the spine will create tension in the flanges 74, 76 which will by virtue of the interdigitation impose a compressive load on the prosthetic disc.

Many of the benefits of the present invention stem from the manner in which the properties of the prosthesis directly correspond to features of the natural disc replaced. The prosthesis in effect mimics a natural disc to a large extent. The deformable core (or insert or block), insert or block performs a very similar function to the nucleus pulposis. The fabric encapsulation performs a very similar function to the annulus. The flanges perform a very similar function to the anterior longitudinal ligament extending down the front of the spine.

The pattern of FIG. 9 may be cut out of a preformed fabric but it is preferably formed using embroidery which can optimally position the fibres within the fabric to maximize the load bearing potential of the construction.

FIGS. 10 and 11 are further illustrations of the embodiment of prosthetic disc 24 illustrated in FIGS. 8 and 9. The prosthetic disc 24 comprises a fabric encapsulation sheath 56 dimensioned to contain a internal core of resilient but suitably deformable material. Flanges 74, 76 extend from the sheath 56 and are interdigitated, in the manner outlined above, by passing the flange 74 through the aperture 80 in the flange 76. In the illustration the flanges 74, 76 each taper outward from a reduced width where they interdigitate to an increased width towards the anchor receiving apertures 78.

In FIG. 12, the embodiment of prosthetic disc 24 shown in FIG. 8 has an additional fabric element 100 added over the front of the device, in a manner similar to that shown in FIG. 6. This additional fabric element 100 may be either a continuation of the upper flange 76 or lower flange 74 (as shown), or may comprise a separate fabric element. The additional fabric element 100 acts to increase the torsional resistance of the prosthetic disc 24. It limits the compression of the elastomeric core resulting from the tension in the flanges 74, 76 when the spine is placed in extension and it also is a barrier to prevent the backing-out of bone screws (not shown) used to secure the flanges 74, 76 to the vertebral bodies 20, 22.

FIG. 13 shows a similar plan view to that shown in FIG. 9 but with the addition of the fabric 100 to be attached over the front of the construction when in situ.

Figure 14:
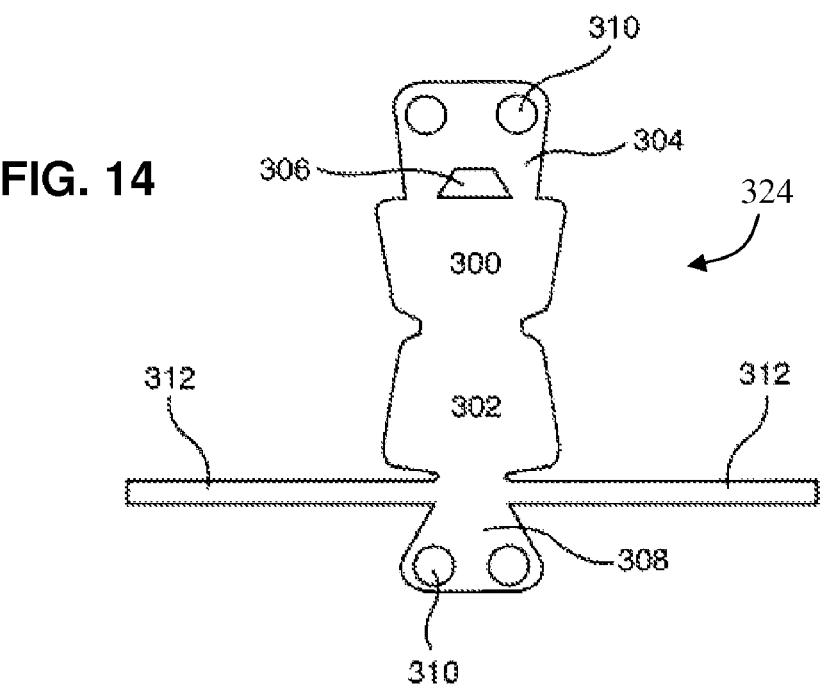
FIG. 14 illustrates a plan view of the fabric profile of a further embodiment of the invention.

FIG. 14 represents in plan view the fabric component prior to assembly of one example of a prosthetic disc 324 similar to that shown in FIGS. 10 & 11. Faces 300 and 302 face one another and contact the core in use. Flange 304 is provided with an aperture 306 through which the opposing flange 308 is interdigitated in use. Apertures 310 are provided in the flanges 304, 308 to accommodate the anchors.

This embodiment of the invention also includes laterally extending arm portions 312 made of the fabric material. In use, these arm portions are folded into multiple folds to provide the cushion pad between the interdigitation location and the core.

Figure 15:
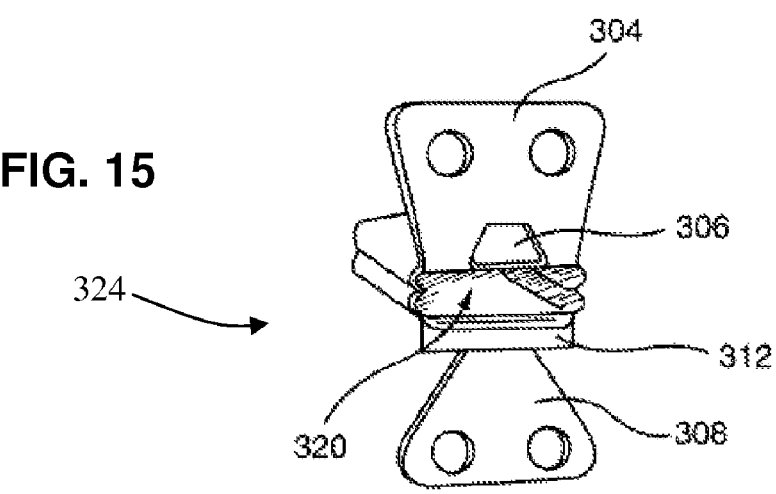
FIG. 15 illustrates the fabric profile of FIG. 14 in a part assembled state, prior to insertion of the core.
Figure 16:
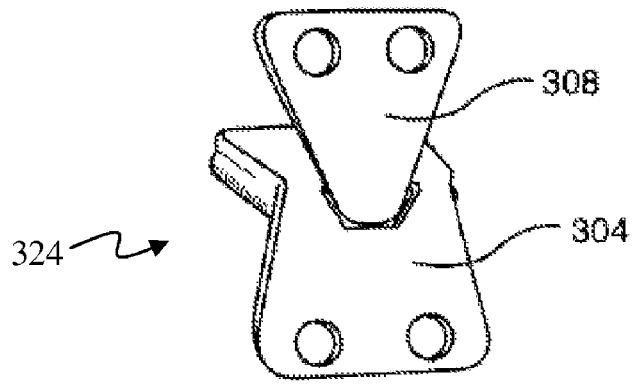
FIG. 16 illustrates the embodiment of FIG. 14 in a final assembled form.

FIG. 15 illustrates the fabric encapsulation of FIG. 14 in its assembled state prior to the insertion of the core. The arms 312 are folded in on one another to provide a cushion mounted on the lower flange 308. Once assembled in this configuration the core (not shown) is inserted into the internal space 320. Following core insertion, the lower flange 308 is passed up through the aperture 306 in the upper flange 304. This pushes the folded pad 312 across the aperture leading to the core and provides a cushion for the core. Once fully interdigitated the structure resumes the format illustrated in FIG. 16.

Figure 17:
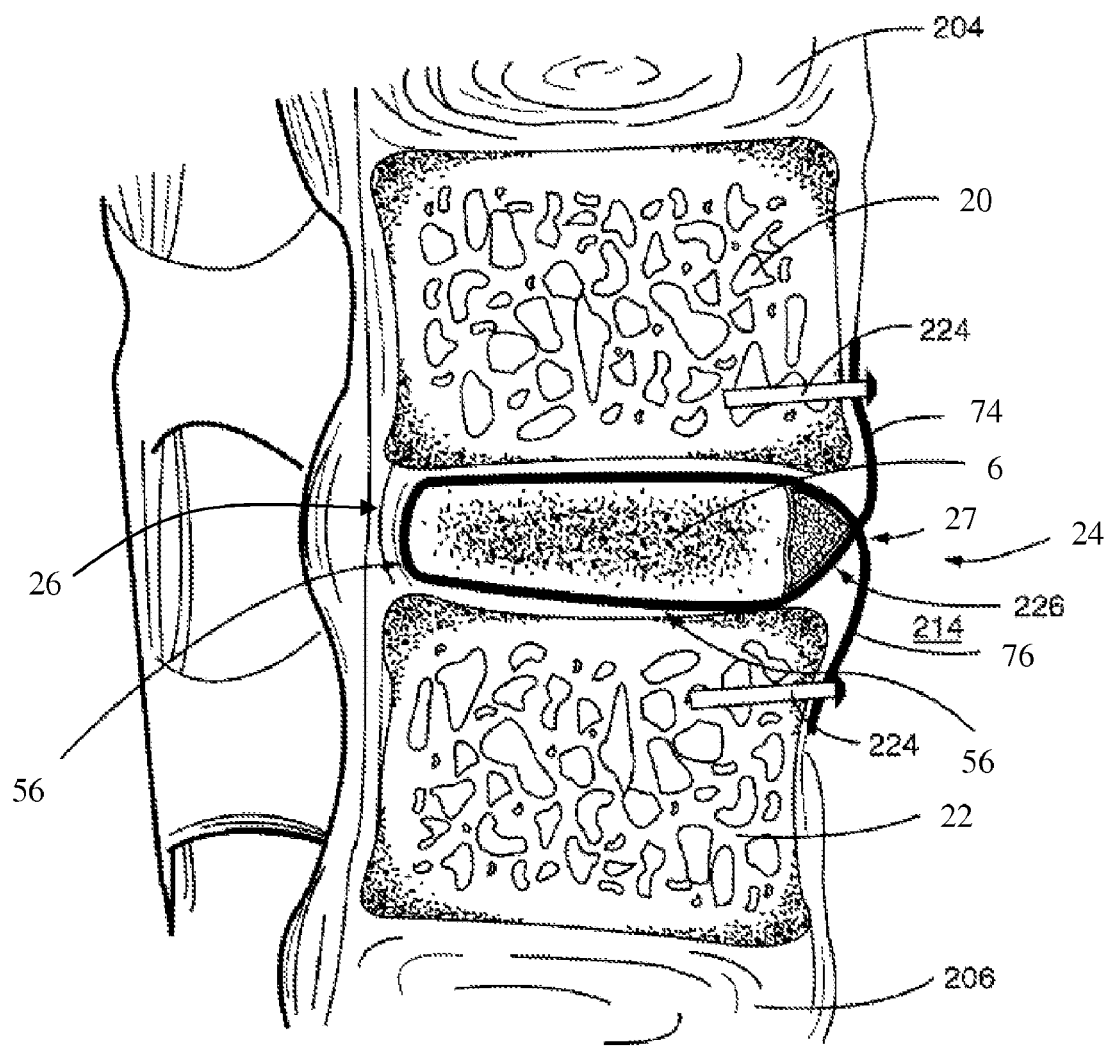
FIG. 17 illustrates the prosthesis of FIGS. 10 and 11 in situ in a spine, in cross section.

In use the pad 312 provides the benefits outlined above in relation to FIG. 17 by promoting retention of the core within the disc space. The pad provides complete encapsulation of the core and also ensures that the edge of the core is held back from the front edge of the disc space. This hold back is beneficial in ensuring that no block to the full flexion of the vertebrae adjacent to the disc space. The risk of the front edge of the prosthesis being nipped by the front edge of the disc is also reduced.

The prosthesis structures provided according to the present invention enable a more natural movement to be provided in spines where disc damage would normally necessitate fusion and no mobility at that location or the provision of a vacant disc space and hypermobility at that location. The prosthesis is closely matched to a natural disc in terms of disc height, stiffness in compression and three planes of rotation, viscoelastic behavior and the transmission of physiological stress to adjacent vertebrae.

Prostheses of the present invention are also beneficial over those used in the prior art in terms of their ease of positioning, tolerance in positioning and in terms of the physiological nature and extent of the movement provided. Behavior more closely replicating natural discs is provided.

It is a particularly important benefit of the present invention that the effects of introducing a prosthesis according to the invention on the adjacent motion segment of the spine are far less pronounced. Problems with increasing the rate of damage or problem formation in the adjacent discs are thus avoided too.

Whilst allowing physiological axial rotation, horizontal gliding and vertical distraction the structure of the prosthesis provides suitable constraints to excessive movement.

These benefits are provided with a prosthesis formed of materials which have proven biocompatibility in other applications, sufficient mechanical endurance and avoid wear particle formation.

Whole cervical spine and single motion segment cadaveric testing have confirmed the more natural movement achieved, both in the spine as a whole and in the individual joint. Fatigue testing over a million cycles indicated no damage to the fibre encapsulation or to the insert itself.

Figure 18:
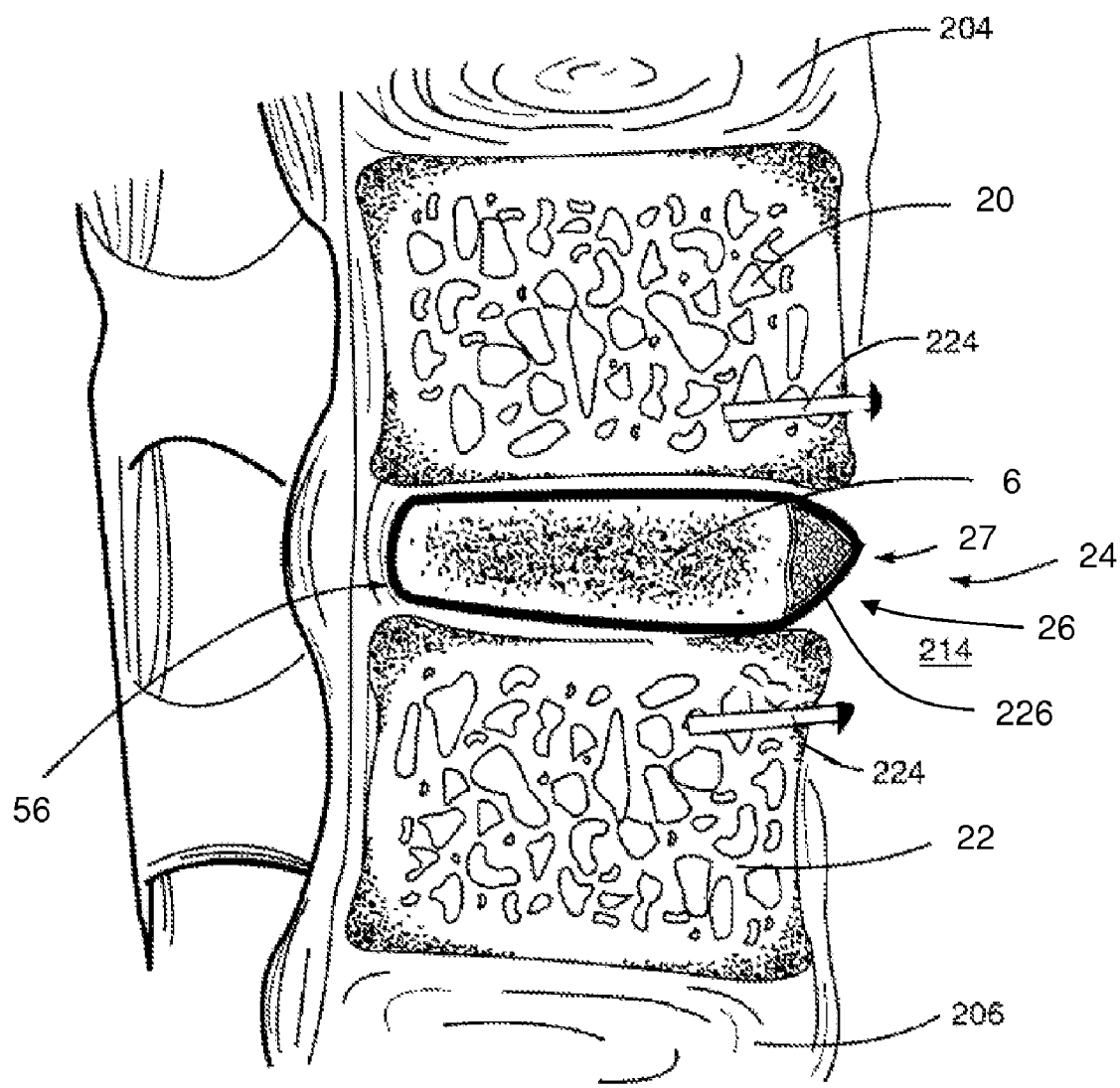
FIG. 18 illustrates the prosthesis of FIGS. 10 and 11 in situ in a spine, in cross section after the flanges have been resorbed.

As previously noted, in some instances it may be advantageous to introduce a prosthesis such as described above, but with flange portions that are bioresorbable such that over time the flange portions are resorbed leaving only the core contained within the encapsulation fabric positioned in the intervertebral space. Referring to FIGS. 17-18, the prosthesis 24 is provided according to the form illustrated in FIGS. 10 and 11 and comprises a visco-elastic core 6, of greater thickness near the insertion side 214 than away from the insertion side 214. This conforms to the natural shape of the space between the vertebrae 20 and 22. The core 6 is encased in the encapsulation fabric 56 in the manner described above. The flanges 74 and 76 extending from the disc space 26 are interdigitated at location 27 and fixed by bone anchors 224. The prosthesis is provided with a fabric pad 226 between the interdigitation location 27 and the core 6. This promotes the correct positioning of the core 6 relative to the vertebrae 20, 22 and the overall prosthesis 24 when the spine is in both flexion and extension. By providing the pad 226 this extension of the spine tends to pull the flanges 74, 76 apart and so squeeze the pad 226 towards the interior of the disc space holding the core 6 in position.

When the spine is in flexion, the pad 226 holds the core 6 away from the front of the disc space 26 where the compression force exerted by the vertebrae 20 and 22 is greatest. The pad 226 may be provided as a distinct element, as shown, which is introduced during assembly, or more preferably, the type of construction illustrated in FIGS. 14-16 may be provided.

In either case, it may be advantageous to provide the encapsulation fabric 56 in a non-bioresorbable fabric and at least one of the flanges 74, 76 in a bioresorbable fabric, such that the flanges are resorbed over time. FIG. 18 illustrates such a prosthetic disc 24 after the flanges have been resorbed over time, leaving only the core 6 encased in encapsulation fabric 56 in the intervertebral space 26.

Figure 19:
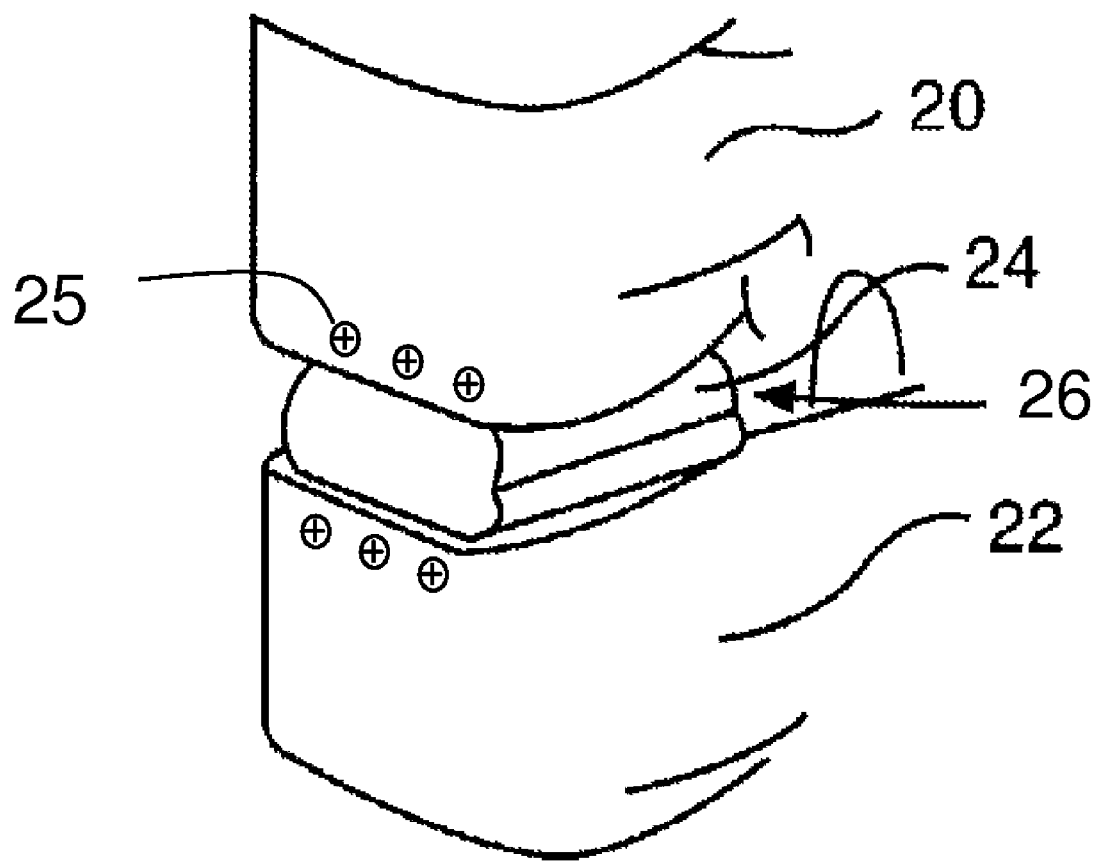
FIG. 19 is a perspective view of an embodiment of FIG. 6, 7, or 8, a prosthetic implant between two vertebrae after the encapsulating fabric and flanges have resorbed.

FIG. 19 represents an alternate embodiment of the prosthetic disc 24 of the present invention, for example such as one shown in any of FIGS. 6-8, after the flanges have been resorbed over time. Thus, the only parts of the prosthetic disc 24 that remain are the core (not shown) and encapsulation fabric 56 surrounding the core, both residing in the intervertebral space 26. Attachment screws 25 also remain as inserted into the vertebral bodies 20, 22.

A prosthetic implant such as the one shown and described above can be modified to fit any number of other types of joints. FIG. 20 shows an example of a prosthetic facet implant 110 according to one embodiment of the present invention. The implant 110 includes a core 112 (FIG. 20A) disposed within an encapsulating jacket 114 having a plurality of flanges 116 extending therefrom. The core may be an elastomeric core as described by way of example above, or may be textile-based as shown and described in PCT Application Serial No. PCT/US2008/068868, filed Jun. 30, 2008 and entitled "Facet Joint Spacer and Related Methods," the entire contents of which are hereby incorporated by reference into this disclosure as if set forth fully herein. In the example shown in FIG. 20, the jacket 114 includes a body portion 118 that at least partially surrounds the core 112. The attachment flanges 116 extend from one end of body portion 118 such that upon insertion within a facet joint, the flanges 116 will all extend outside the joint in a similar manner. The body portion 118 is sized and dimensioned to receive the prosthetic core 112 (e.g. elastomeric or textile) such as is shown and described by way of example above. The flanges 116 function to provide a vehicle for attachment of the implant 110 to the superior and/or inferior facets, thereby securing the body portion 118 containing the core 112 with the facet joint. The flanges 116 may be attached to adjacent vertebrae using any suitable means of attachment, for example including but not limited to bone screws, staples, sutures, nails, buttons, anchors, and/or adhesives.

As discussed above, it may be advantageous to provide an implant having flanges 116 that are composed of bioresorbable fabric such that over time the fabric resorbs, leaving only the core and encapsulation fabric residing in the facet joint. This feature may provide for greater mobility of the facet over time, and thus succeed in mimicking normal physiology. Accordingly, the encapsulating jacket 114 of the implant 110 includes a portion (e.g. a strip) of bioresorbable fabric 120 on each flange 116 adjacent to the body portion 118. As such, over time the bioresorbable fabric 120 will disappear, causing the body portion 118 and flanges 116 to become detached from one another.

FIG. 21 illustrates the placement of the prosthetic facet implant 110 including bioresorbable portions 120 within a facet joint 102 forming part of the lumbar spine, before the flanges 116 have been attached to bone. The facet joint 102 exists between the superior facet 104 (forming part of the superior vertebra 20) and the inferior facet 106 (forming part of the inferior vertebra 22). The body portion 118 which holds the prosthetic core 112 is inserted in the facet joint 102, and the flanges 116 extend outward for attachment to vertebrae 20, 22.

Figure 22:
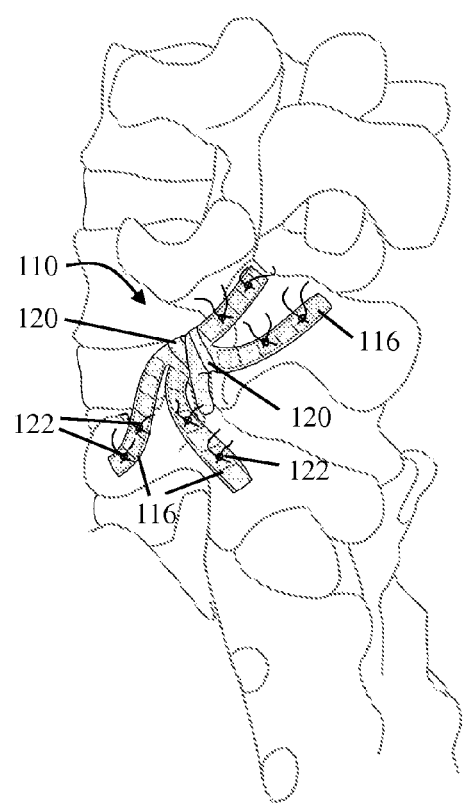
FIG. 22 illustrates the implant of FIG. 21 after the flanges have been secured to adjacent bone tissue, before degradation of the biodegradable fabric portions.

Referring to FIG. 22, flanges 116 of the prosthetic facet implant 110 are attached to adjacent vertebrae 20, 22 through the use of any suitable attachment means described above. By way of example only, the embodiment shown and described in FIG. 22 utilizes sutures 122 for attachment. The flanges 116 may be attached to any suitable portion of the vertebrae, including but not limited to the vertebral body, spinous process, pedicle, lamina, superior and/or inferior facet, and/or any combination thereof.

Figure 23:
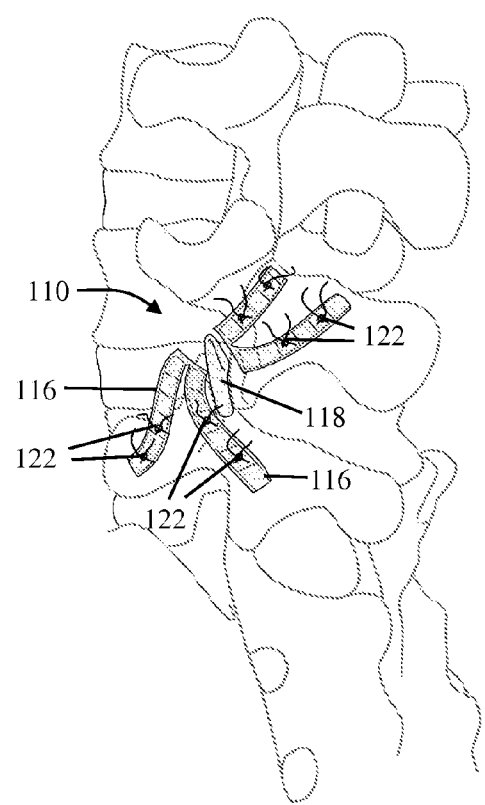
FIG. 23 illustrates the implant of FIG. 22 inserted within a facet joint with flanges secured to adjacent bone tissue, after degradation of the biodegradable fabric portions.

FIG. 23 illustrates the implant 110 in position after resorbtion of the bioresorbable fabric portions 120 has occurred. After time, the body portion 118 containing the core 112 remains positioned between the superior facet 101 and inferior facet 103 (and thus within the facet joint 102). The flanges 116 have become detached from the body portion 118, though they still may be attached to the bone via sutures 122 remaining within the vertebrae 20, 22.

Figure 24:
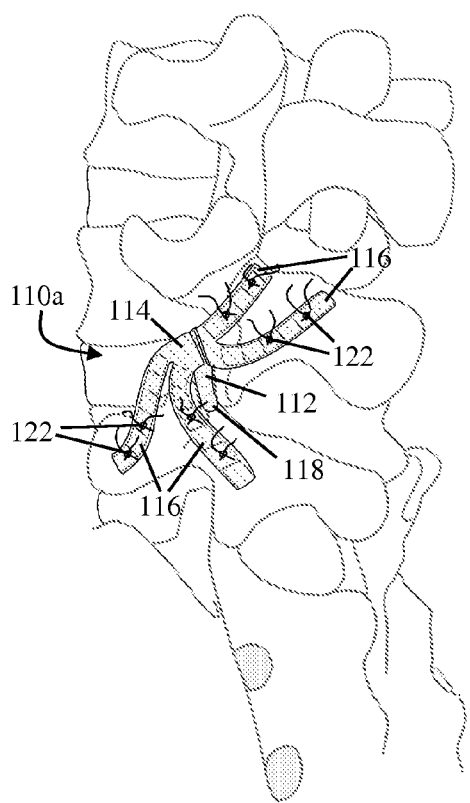
FIG. 24 illustrates an example of a facet implant including a biodegradable fabric jacket according to an alternate embodiment of the present invention, the facet implant inserted into a facet joint and before degradation of the biodegradable fabric jacket.
Figure 25:
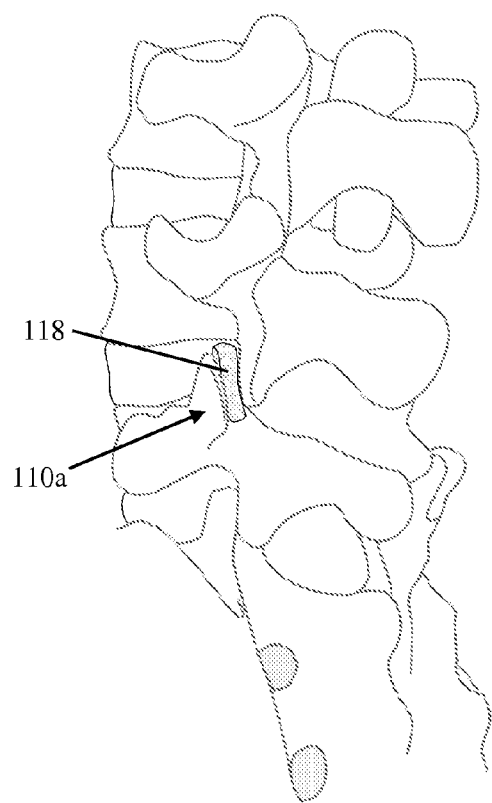
FIG. 25 illustrates the facet implant of FIG. 24 after degradation of the fabric jacket.

FIGS. 24-25 illustrate an example of a facet implant 110a according to an alternative embodiment of the present invention. Implant 110a is similar to implant 110 of FIG. 20, and includes a core 112 and encapsulating jacket 114. In the example shown in FIG. 24, the jacket 114 includes a body portion 118 that at least partially surrounds the core 112. The attachment flanges 116 extend from one end of the body portion 118 such that upon insertion within a facet joint, the flanges 116 will all extend outside the joint in a similar manner. In this example, the portions of the encapsulating fabric 114 forming the flanges 116 are entirely bioresorbable, and after resorbtion only the body portion 118 surrounding the core 112 is left within the facet joint (FIG. 25). In the example shown, sutures 122 are bioresorbable, although it is possible that sutures 122 (or any other attachment element used to attach flanges 116 to the vertebrae) are not bioresorbable without departing from the scope of the present invention.

Regarding the methods of using all examples of spinal implants disclosed herein, it will be understood that several method steps are inherent to performing surgery, and thus have been omitted from each description of use above. However, these steps may be integral in the use of the devices disclosed herein, including but not limited to creating an incision in a patient's skin, distracting and retracting tissue to establish an operative corridor to the surgical target site, advancing the implant through the operative corridor to the surgical target site, removing instrumentation from the operative corridor upon insertion of the implant into the target facet joint, and closing the surgical wound.

Figure 26:
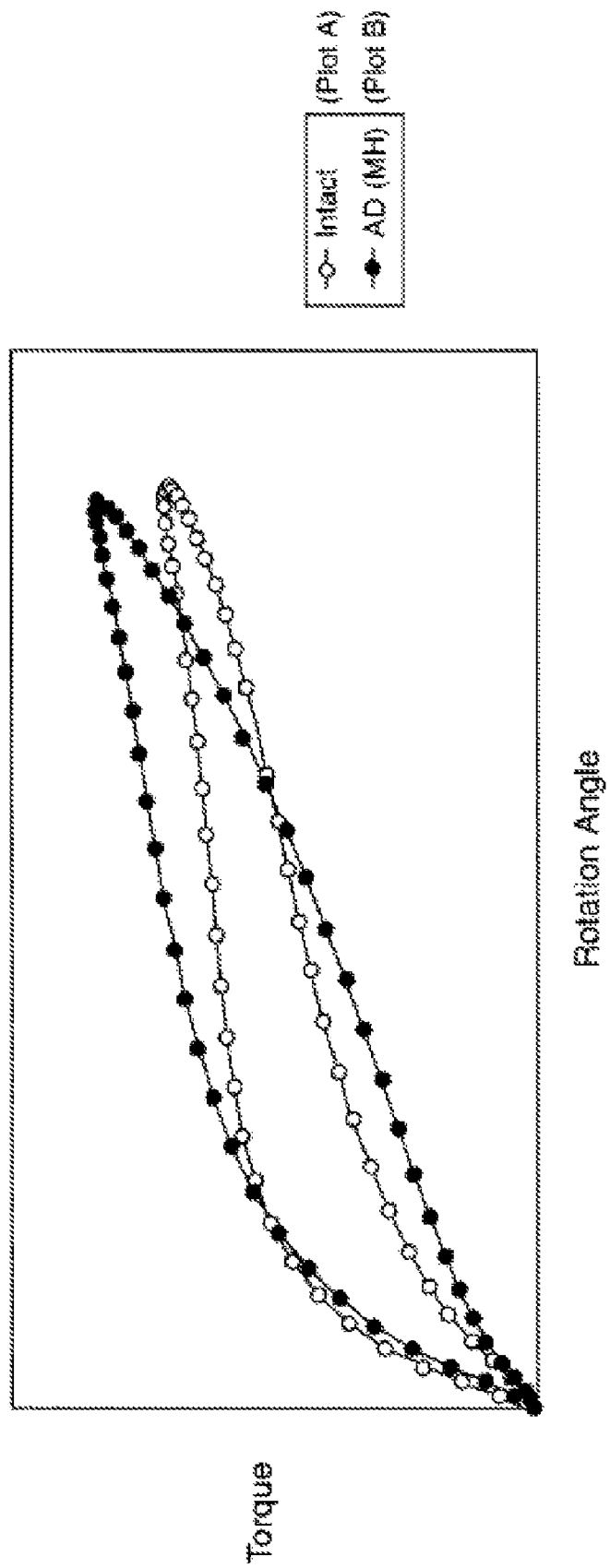
FIG. 26 illustrates the torque against rotational angle results for a sagittal rotation test on a monosegment C4/5.

FIG. 26 illustrates the hysteresis loop for sagittal rotation of a C4/C5 joint with a natural disc, plot A, (the arrows indicate the direction of flexure, left to right for forward, right to left for back) and for a disc according to the present invention, plot B. As can clearly be seen the plots very closely match one another reflecting the near equivalence of the prosthesis to the natural disc during such movement. The deviation between the plots is similar to the variation arising between two natural discs.

Figure 27:
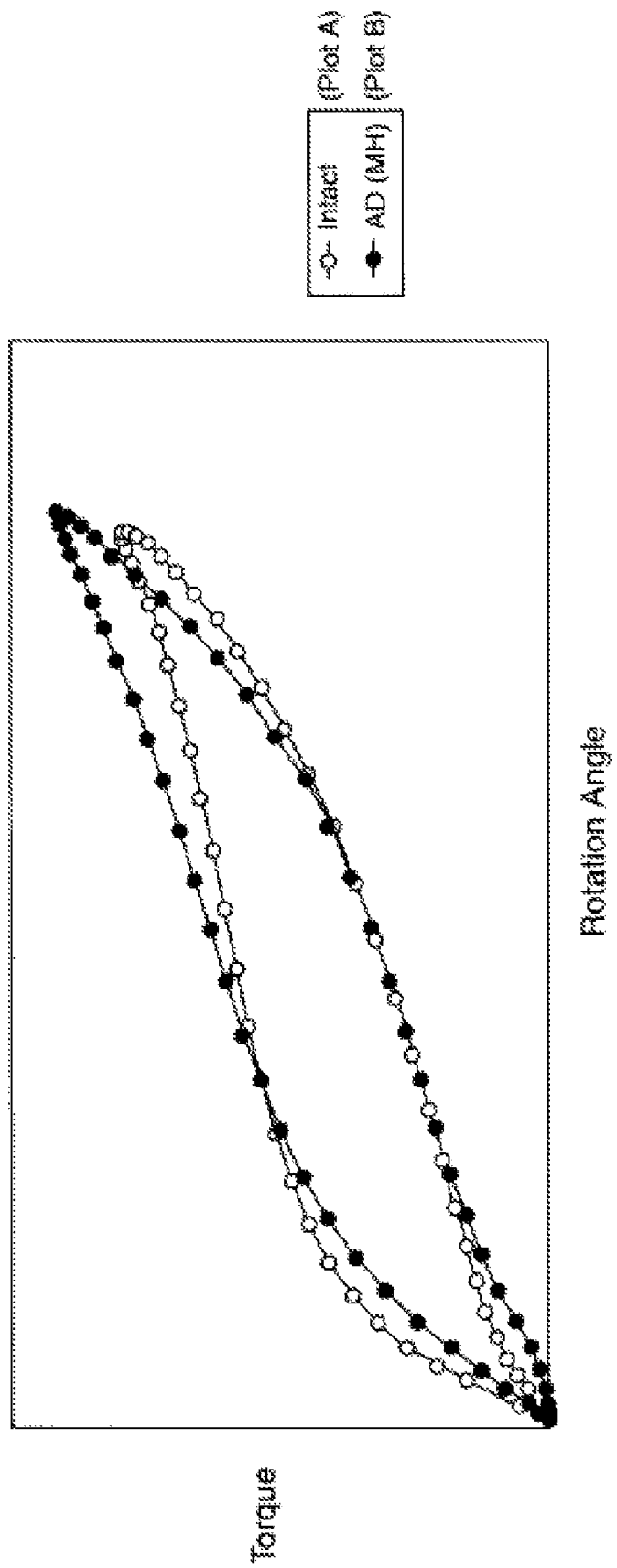
FIG. 27 illustrates the torque versus rotational angle results for a lateral rotational test on a C4/5 monosegment.

FIG. 27 shows a similar set of hysteresis plots for a natural disc, plot A, and a prosthesis according to the invention, plot B, during a lateral rotation test, again illustrating the near equivalence in performance.

Multi-segment evaluation of the prosthesis also indicated that the position of the centre of rotation was very similar when a prosthesis according to the present invention was deployed, when compared with a fully natural disc multi-segment test.

Similarly the % contribution to the movement was a far closer match between the present invention's prosthesis and a natural disc, than between any of the prior art prosthesis or surgical techniques and a natural disc multi-segment.

Over and above these advantages, if the prosthesis should fail for some reason, it is far easier to remove to the necessary extent to enable a fusion (the recognized follow up treatment for a failed prosthesis) to be performed. The present invention merely needs the fabric to be cut to an extent enabling the core to be removed. The fabric flanges can be left in-situ, avoiding problems where, for instance, significant tissue ingrowth has occurred. Tissue ingrowth on the flanges may be avoided by providing an in-growth retarding coating to these parts. Implants provided with optional bioresorbable flanges as described herein avoid this problem altogether, as the flanges are resorbed over time.

We claim:

1. A method of performing spine surgery, comprising:
creating an operative corridor to access a surgical target site within a spine;
implanting a biocompatible prosthesis, said prosthesis comprising a core element at least partially encapsulated by a non-bioresorbable textile jacket, the jacket comprising a body portion having a pair of opposing vertebral contact surfaces configured to contact a surface of a vertebral body, and at least one textile flange extending from said body portion, at least a portion of said flange having a bioresorbable portion formed from bioresorbable fibers, said at least one flange having an aperture through which an opposing flange is interdigitated during use, said body portion of said prosthesis implanted within said surgical target site;
attaching said flange to a bone segment adjacent said surgical target site; and
closing said operative corridor.

2. The method of claim 1, wherein said core is formed from at least one of silicon rubber, elastomer, hydrogel, hydrogel beads, plastic mesh, plastic constructs, injectable fluids, curable fluids, polyester fiber, polypropylene, polyethylene, ultra high molecular weight polyethylene (UHMWPe), polyether-ether-ketone (PEEK), carbon fiber, glass, glass fiber, polyaramide, metal, copolymers, polyglycolic acid, polylactic acid, biodegradable fibers, nylon, silk, cellulosic and polycaprolactone fibers.

3. The method of claim 1, wherein said at least one of textile jacket and said flange is at least partially formed from at least one of polyester fiber, polypropylene, polyethylene, ultra high molecular weight polyethylene (UHMWPe), polyether-ether-ketone (PEEK), carbon fiber, glass, glass fiber, polyaramide, metal, copolymers, polyglycolic acid, polylactic acid, nylon, silk, cellulosic and polycaprolactone fibers.

4. The method of claim 1, wherein at least one of said core, textile jacket, and flange is formed using embroidery, weaving, three-dimensional weaving, knitting, three-dimensional knitting, injection molding, compression molding, cutting woven fabrics and cutting knitted fabrics.

5. The method of claim 1, wherein said bioresorbable portion comprises a band of fibers at a proximal end of said flange near an interface with said body portion, said band extending across and through said flange such that upon resorbtion of said bioresorbable portion, said flange is disconnected from said body portion.

6. The method of claim 1, wherein said bioresorbable portion comprises the entire flange.

7. The method of claim 1, wherein the attaching is accomplished using an attachment member configured to attach said flange to bone, said attachment member comprising at least one of a bone screw, staple, suture, nail, button, anchor, and/or adhesive.

8. The method of claim 7, wherein said attachment member is made from a bioresorbable material.

9. The method of claim 1, wherein said surgical target site comprises at least one of an intervertebral space and an intrafacet space.

10. The method of claim 1, wherein said textile jacket is sufficiently porous to allow for at least one of tissue and bony ingrowth at least partially therethrough.

* * * * *